United States Patent
Michel et al.

(10) Patent No.: US 12,372,669 B2
(45) Date of Patent: Jul. 29, 2025

(54) FRONT-END ELECTRONIC CIRCUITRY FOR A PHOTON COUNTING APPLICATION

(71) Applicant: ams International AG, Jona (CH)

(72) Inventors: Fridolin Michel, Au (CH); Charalambos Andreou, Tann (CH); Massimo Rigo, Munich (DE); Matthias Steiner, Seiersberg (AU); Juan Miguel Gavillero, Paterna (ES)

(73) Assignee: AMS SENSORS SINGAPORE PTE. LTD., Singapore (SG)

( * ) Notice: Subject to any disclaimer, the term of this patent is extended or adjusted under 35 U.S.C. 154(b) by 153 days.

(21) Appl. No.: 18/251,784

(22) PCT Filed: Nov. 3, 2021

(86) PCT No.: PCT/EP2021/080506
§ 371 (c)(1),
(2) Date: May 4, 2023

(87) PCT Pub. No.: WO2022/101071
PCT Pub. Date: May 19, 2022

(65) Prior Publication Data
US 2023/0417932 A1    Dec. 28, 2023

(30) Foreign Application Priority Data
Nov. 12, 2020  (DE) .................. 10 2020 129 875.7

(51) Int. Cl.
*G01T 1/20* (2006.01)
*A61B 6/42* (2024.01)

(52) U.S. Cl.
CPC .............. *G01T 1/20* (2013.01); *A61B 6/4241* (2013.01)

(58) Field of Classification Search
CPC .......... G01T 1/20; G01T 1/171; A61B 6/4241
See application file for complete search history.

(56) References Cited

U.S. PATENT DOCUMENTS

| 7,480,362 B2 | 1/2009 | Carmi |
| 10,180,351 B2 | 1/2019 | Viswanath et al. |

(Continued)

FOREIGN PATENT DOCUMENTS

| EP | 3 385 756 A1 | 10/2018 |
| JP | 2013-506822 A | 2/2013 |

(Continued)

OTHER PUBLICATIONS

Notice of Reasons for Rejection issued in corresponding Japanese Patent Application No. 2023-525534 dated May 17, 2024, with English language translation, 13 pages.

(Continued)

*Primary Examiner* — Kiho Kim
(74) *Attorney, Agent, or Firm* — MH2 Technology Law Group LLP

(57) ABSTRACT

A front-end electronic circuitry for a photon counting application includes a charge sensitive amplifier including an amplifier circuit and a capacitor being arranged in a feedback path between the input side and the output side of the amplifier circuit. A controllable switch is arranged in parallel to the capacitor. The circuitry includes a delay circuit to provide a delay circuit output signal being a time-delayed representation of the charge sensitive amplifier output signal. An output signal generation circuit is configured to generate the output signal by subtracting the delay circuit output signal from the charge sensitive amplifier output signal.

15 Claims, 4 Drawing Sheets

(56) References Cited

U.S. PATENT DOCUMENTS

| | | | |
|---|---|---|---|
| 2004/0017224 A1* | 1/2004 | Tumer | H04N 25/773 |
| | | | 327/51 |
| 2010/0207027 A1 | 8/2010 | Marks et al. | |
| 2011/0098980 A1 | 4/2011 | Ouvrier-Buffet et al. | |
| 2014/0264050 A1 | 9/2014 | Rostaing et al. | |
| 2016/0076935 A1* | 3/2016 | Daerr | G01T 1/171 |
| | | | 250/214 R |
| 2017/0035376 A1 | 2/2017 | Surendranath et al. | |
| 2019/0064373 A1 | 2/2019 | Cao et al. | |
| 2020/0064500 A1 | 2/2020 | Steadman Booker et al. | |

FOREIGN PATENT DOCUMENTS

| | | |
|---|---|---|
| JP | 2020-516878 A | 6/2020 |
| WO | 2008155680 A2 | 12/2008 |
| WO | 2009050619 A2 | 4/2009 |
| WO | 2018185118 A1 | 10/2018 |

OTHER PUBLICATIONS

Eberle, K. (Authorized Officer), International Search Report and Written Opinion dated Jan. 26, 2022, PCT Application No. PCT/EP2021/080506, 11 pages.

Beller; German Search Report issued in DE Patent Application No. 102020129875.7 dated Jul. 15, 2021, 6 pages.

Lee, D. et al., "Energy-correction photon counting pixel for photon energy extraction under pulse pile-up", Nuclear Instruments & Methods in Physics Research. Section A, Elsevier BV North Holland, NL, vol. 856, Feb. 28, 2017 (Feb. 28, 2017), pp. 36-46, XP029977360,.

Gustavsson, M. et al., "A high-rate energy-resolving photon-counting ASIC for spectral computed tomography", IEEE Transactions on Nuclear Science 59.1 (2011), pp. 30-39.

\* cited by examiner

FRONT-END ELECTRONIC CIRCUITRY FOR A PHOTON COUNTING APPLICATION

CROSS-REFERENCE TO RELATED APPLICATIONS

The present application is the national stage entry of International Patent Application No. PCT/EP2021/080506, filed on Nov. 3, 2021, and published as WO 2022/101071 A1 on May 19, 2022, which claims the benefit of priority of German Patent Application No. 10 2020 129 875.7, filed on Nov. 12, 2020, the disclosures of all of which are incorporated by reference herein in their entireties.

TECHNICAL FIELD

The disclosure relates to a front-end electronic circuitry which may be used in a photon counting application, such as multi-energy spectral CT (Computed Tomography). The disclosure further relates to a photon counting circuitry, and a device for medical diagnostics.

BACKGROUND

In conventional Computed Tomography applications, an indirect detection principle is used to detect a photon which passes easily through soft tissues of a body of a patient. Indirect detectors comprise a scintillator to convert X-rays to visible light which is captured by a photodetector or photodiode to provide an electrical signal in response to the X-rays impinging on the material of the scintillator. As opposed to conventional Computed Tomography using the indirect detection principle, photon counting Computed Tomography resorts to direct conversion sensors. Direct conversion sensors use a particular material, for example CdTe, CdZnTe, Si, GaAs, TlBr, etc., to generate electron-hole pair clouds in response to the interaction of an X-ray photon within the bulk. The amount of charge is proportional to the energy of the impinging photon.

Electrons—for the case of a material of CdTe/CZT, for example—induce a transient current signal on their collecting electrode (anode) which is then further processed by front-end electronics. The front-end generates a voltage pulse with amplitude proportional to the energy of the impinging photon. The amplitude of the voltage pulse is then compared to a plurality of energy discriminators. The discriminators with an energy threshold lower than the pulse amplitude toggle and increment a corresponding counter. The number of photons per energy are counted in the discriminators within time intervals (image projections).

FIG. 1 shows a block diagram of a photon counting circuitry 2 comprising a front-end electronic circuit 10, a photon detector 20 and an energy discriminator 30. The photon detector 20 generates a transient current pulse $I_{pulse}$ caused by a photon impinging a photosensitive area 21 of the photon detector 20. The front-end electronic circuitry 10 usually comprises a charge sensitive amplifier and a shaper stage. The shaper stage generates a voltage pulse amplitude proportional to the energy (charge) of the impinging X-ray photon. The charges provided by the current pulse $I_{pulse}$ are integrated and removed again as fast as possible by the shaper stage in order to accommodate the next interaction, which is random in time. The amplitude of the voltage pulse Vpulse generated by the shaper stage is compared against a number of energy thresholds of discriminators of the energy discriminator 30 to count and categorize every photon according to its energy.

For Computed Tomography applications, the X-ray flux may be in excess of $1*10^9$ photons/mm²s. Very high counting rates are therefore required, driving the design of the front-end electronic circuitry 10 to operate in very high ballistic deficit conditions.

Ballistic deficit is the loss of pulse amplitude compared to ideal full collection, related to the continuous discharge of a feedback capacitor of the charge sensitive amplifier of the front-end electronic circuitry 10. In conclusion, the maximum of the voltage pulse Vpulse does not reach the theoretical C/Q value due to the simultaneous discharge through a resistor being connected in parallel to the feedback capacitor of the charge sensitive amplifier. A feedback resistor (or other discharging mechanisms) is required to shape the pulse and bring the voltage back to the reference in order to be able to process a subsequent pulse as fast as possible.

Ballistic deficit plays an important role in the energy resolution of photon counting detectors. Events with the same impinging X-ray energy may manifest slightly different transient responses on the detector depending on the location of the event (relative to the center of the pixels and depth of interaction). Electronics for very high count-rates must typically operate at high-ballistic deficit conditions.

Working in such conditions entails that the front-end electronic circuitry delivers slightly different pulse amplitudes of the voltage signal Vpulse for events with the same energy but different location of the interaction. This contributes to an uncertainty of the registered energy, which leads to a worse energy resolution.

There is a need to provide a front-end electronic circuitry for a photon counting application capable of operating at very high count rates while exhibiting negligible ballistic deficit, leading to a better performance. Furthermore, there is a desire to provide a photon counting circuitry having high performance regarding counting rates and energy resolution. Moreover, there is a desire to provide a device for medical diagnostics capable to operate at very high count rates.

SUMMARY

A front-end electronic circuitry for a photon counting application having reduced ballistic deficit and enabling high photon count rates is specified in claim 1.

The front-end electronic circuitry comprises an output node to provide an output signal, an input node to receive an input signal, a charge sensitive amplifier comprising an amplifier circuit having an input side being coupled to the input node and an output side to provide a charge sensitive amplifier output signal, and a capacitor being arranged in a feedback path between the input side and the output side of the amplifier circuit. The front-end electronic circuitry further comprises a controllable switch being arranged in parallel to the capacitor, and a delay circuit to provide a delay circuit output signal. The delay circuit output signal is a time-delayed representation of the charge sensitive amplifier output signal. The front-end electronic circuitry comprises an output signal generation circuit being coupled to the output node to provide the output signal. The output signal generation circuit is configured to generate the output signal by subtracting the delay circuit output signal from the charge sensitive amplifier output signal.

According to a possible embodiment of the front-end electronic circuitry, the delay circuit has an input side to receive the charge sensitive amplifier output signal. The delay circuit is configured to generate the delay circuit output signal with a first delay time after having received the charge sensitive amplifier output signal at the input side of the delay circuit.

According to an embodiment of the front-end electronic circuitry, the amplifier circuit and the capacitor are arranged so that, when the input signal is formed as a current pulse, a charge is stored in the capacitor. The charge is dependent on the current pulse of the input signal.

According to another embodiment of the front-end electronic circuitry, the controllable switch is operated in a non-conductive state and a conductive state. The controllable switch and the capacitor are arranged so that the capacitor is charged when the controllable switch is operated in the non-conductive state, and the capacitor is discharged when the controllable switch is operated in the conductive state.

This configuration allows the front-end electronic circuitry to be provided with a reset topology. The reset topology allows to use a high resistive feedback path which in turn allows ballistic deficit to be reduced while keeping high count-rate capabilities. After each pulse of the input signal received at the input node, and after having the full charge of the input event collected on the capacitor in the feedback path, the charge sensitive amplifier is reset by the controllable switch. The front-end electronic circuitry shows negligible ballistic deficit with no flux-dependent energy distortion other than pulse pile-up.

According to a possible embodiment of the front-end electronic circuitry, the circuitry comprises a control circuit being configured to monitor the charge stored in the capacitor and to control the controllable switch in dependence on the charge stored in the capacitor. In particular, the control circuit is configured to switch the controllable switch from the non-conductive state in the conductive state after a delay, when the control circuit detects that the charge stored in the capacitor exceeds a threshold value.

According to a possible embodiment of the front-end electronic circuitry, the control circuit comprises a second delay circuit to generate a control signal to switch the controllable switch from the non-conductive state into the conductive state. The second delay circuit is configured to generate the control signal with a second delay time after the control circuit has detected the exceeding of a threshold value of the charge stored in the capacitor.

In conclusion, after an input current pulse having energy above a threshold value is detected, a delay is triggered. After the delay has elapsed, the (feedback) capacitor is reset.

According to a possible embodiment of the front-end electronic circuitry, the delay circuit and the second delay circuit are configured such that the second delay time is shorter than or equal to the first delay time. The second delay time is selected such that the worst case charge collection time is considered. The first delay time of the (transient) delay circuit ensures full collection of the charge in the (feedback) capacitor.

According to a possible embodiment, the front-end electronic circuitry comprises a second controllable switch to disconnect the delay circuit from the output signal generation circuit. The output signal generation circuit has a first input connected to the further controllable switch and a second input connected to the output side of the charge sensitive amplifier circuit.

The second controllable switch is configured to be operated in a first state in which the second controllable switch connects the delay circuit to the first input of the output signal generation circuit, and a second state in which the second controllable switch disconnects the delay circuit from the first input node of the output signal generation circuit, and connects the first input node of the output signal generation circuit to a reference potential.

The second controllable switch may be advantageously used to disconnect the delay circuit output signal from the output signal generation circuit by connecting the first input node of the output signal generation circuit to the reference potential. In particular, the second controllable switch is advantageously provided due to the reset of the (feedback) capacitor of the charge sensitive amplifier. The second controllable switch ensures that the propagation of the delay circuit output signal to the signal generation circuit is interrupted, thus eliminating an additional undershoot of the output signal at the output node of the front-end electronic circuitry.

According to a possible embodiment of the front-end electronic circuitry, the control circuit comprises a third delay circuit to generate a second control signal with a first level to switch the second controllable switch from the first state to the second state, and with a second level to switch the second controllable switch from the second state to the first state. The third delay circuit is configured to generate the first level of the second control signal with a third delay time after having generated the second level of the second control signal.

According to an advantageous embodiment of the front-end electronic circuitry, the third delay circuit is configured such that the third delay time is equal or longer than the second delay time. In this case, the output signal at the output node of the front-end electronic circuitry will follow the reset of the (feedback) capacitor of the integrator of the electronic circuitry with no undershoots.

The proposed configuration of the front-end electronic circuitry resolves the trade-off between the count-rate and energy resolution, which is very relevant for clinical applications in Computed Tomography. In addition, the immunity to variations of the input transient response, leads to better overall signal stability.

A photon counting circuitry which allows to detect a large number of photons impinging on a photon detector is specified in claim 14.

The photon counting circuitry comprises a front-end electronic circuitry according to one of the embodiments, as described above, and a photon detector having a photon sensitive area. The photon detector is configured to generate a current pulse, when a photon hits the photon sensitive area.

The photon counting circuitry further comprises an energy discriminator being connected to the output node of the front-end electronic circuitry. The photon detector is connected to the input node of the front-end electronic circuitry so that the current pulse generated by the photon detector circuitry is applied to the input node of the front-end electronic circuitry, when the photon hits the photon sensitive area of the photon detector.

The front-end electronic circuitry is configured to generate a voltage pulse at the output node of the front-end electronic circuitry, when the current pulse is applied to the input node of the front-end electronic circuitry. The energy discriminator is configured to generate a digital signal in dependence on a level of the voltage pulse.

A device for medical diagnostics using the principle of photon counting is specified in claim 15. The device comprises the photon counting circuitry, as specified above. The device may be configured as an X-ray apparatus or as a computer tomography.

Additional features and advantages of the front-end electronic circuitry are set forth in the detailed description that follows. It is to be understood that both the foregoing general description and the following detailed description are merely exemplary, and are intended to provide an overview or framework for understanding the nature and character of the claims.

BRIEF DESCRIPTION OF THE DRAWINGS

The accompanying drawings are included to provide further understanding, and are incorporated in, and constitute a part of, the specification. As such, the disclosure will be more fully understood from the following detailed description, taken in conjunction with the accompanying figures in which.

DETAILED DESCRIPTION OF THE EMBODIMENTS

Figure 1:
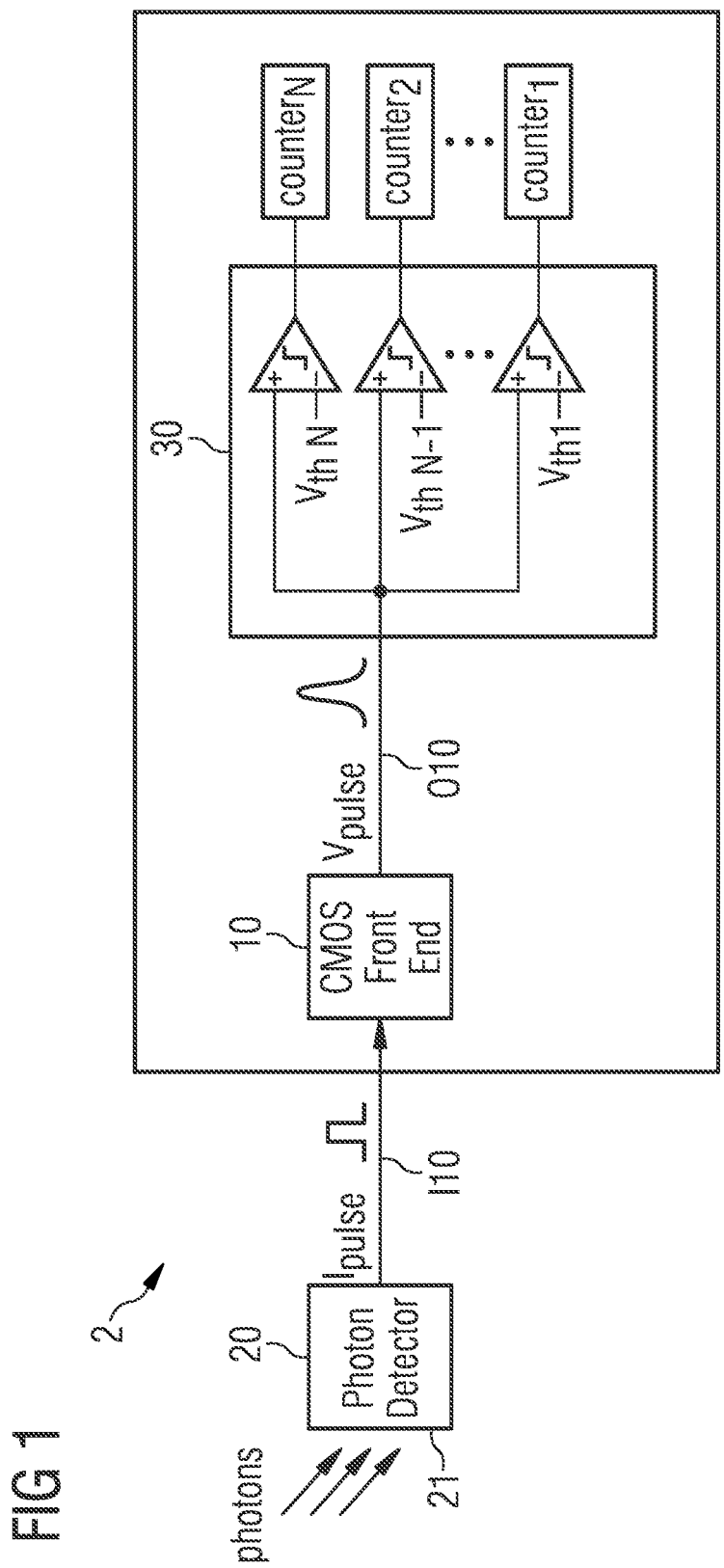
FIG. 1 shows a block diagram of a photon counting circuitry.
Figure 2A:
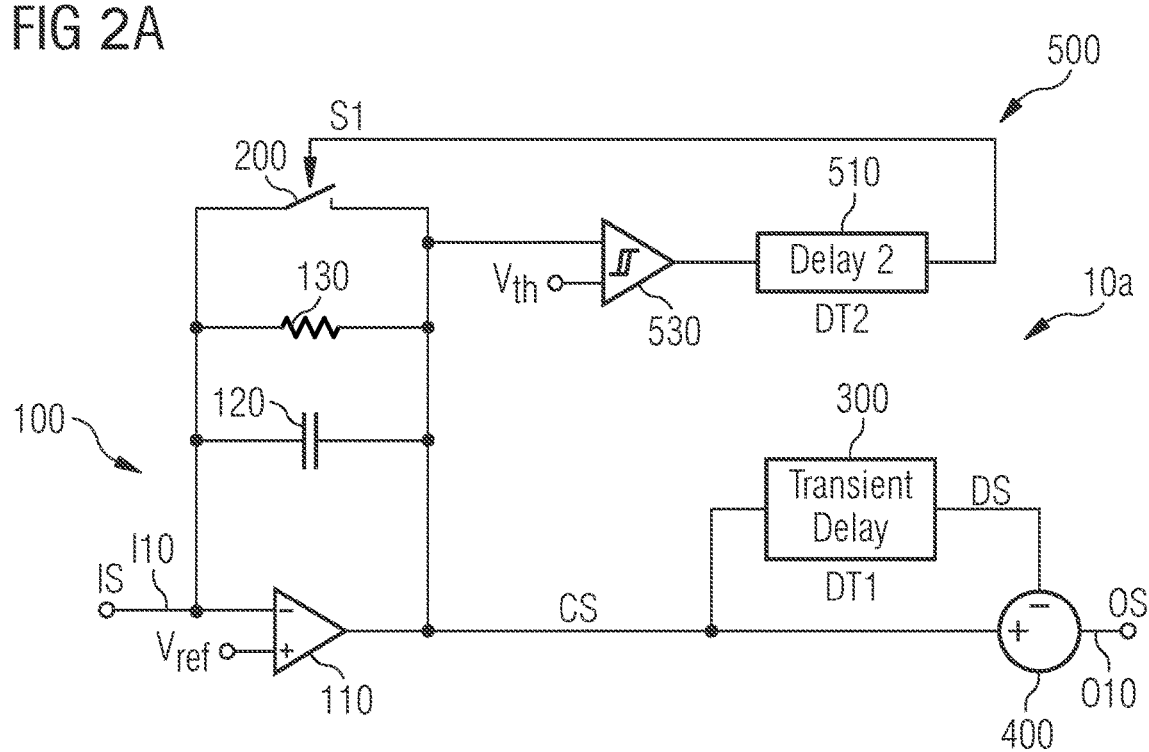
FIG. 2A illustrates a first embodiment of a front-end electronic circuitry for a photon counting application having reduced ballistic deficit and high count-rate capabilities.

FIG. 2A shows an embodiment of a front-end electronic circuitry 10a for generating an output signal OS configured as a voltage pulse in response to an input transient current, for example a current pulse generated by a photon detector 20 shown in FIG. 1. The front-end electronic circuitry 10a comprises an output node O10 to provide the output signal OS and an input node I10 to receive an input signal IS. The front-end electronic circuitry further comprises a charge sensitive amplifier 100 comprising an amplifier circuit 110 having an input side being coupled to the input node I10 and an output side to provide a charge sensitive amplifier output signal CS. The charge sensitive amplifier 100 further comprises a (feedback) capacitor 120 being arranged in a feedback path between the input side and the output side of the amplifier circuit 110. The charge sensitive amplifier 100 may optionally include a (feedback) resistor 130 being connected in parallel to the capacitor 120.

The front-end electronic circuitry 10a further comprises a controllable switch 200 being arranged in parallel to the capacitor 120. Moreover, the front-end electronic circuitry 10a comprises a delay circuit 300 to provide a delay circuit output signal DS. The delay circuit output signal DS is a time-delayed representation of the charge sensitive amplifier output signal CS. The front-end electronic circuitry 10a comprises an output signal generation circuit 400 being coupled to the output node O10 to provide the output signal OS. The output signal generation circuit 400 is configured to generate the output signal OS by subtracting the delay circuit output signal DS from the charge sensitive amplifier output signal CS. According to a possible embodiment, the output signal generation circuit 400 is configured as a signal adder.

The amplifier circuit 110 and the capacitor 120 are arranged so that, when the input signal IS is formed as a current pulse, for example a current pulse $I_{pulse}$ generated by the photon detector 20 shown in FIG. 1, a charge is stored in the capacitor 120, when the controllable switch 200 is in a non-conductive state, as shown in FIG. 2A. The charge stored in the capacitor 120 is dependent on the current pulse of the input signal IS.

The controllable switch 200 is configured to be operated in a non-conductive state and a conductive state. The controllable switch 200 and the capacitor 120 are arranged so that the capacitor 120 is charged, when the controllable switch 200 is operated in the non-conductive state, and the capacitor 120 is discharged, when the controllable switch 200 is operated in the conductive state.

The front-end electronic circuitry 10a comprises a control circuit 500 being configured to monitor the charge stored in the capacitor 120 and to control the controllable switch 200 in dependence on the charge stored in the capacitor 120. According to a possible embodiment of the front-end electronic circuitry, the control circuit 500 is configured to switch the controllable switch 200 from the non-conductive state into the conductive state, when the control circuit 500 detects that the charge stored in the capacitor 120 exceeds a threshold value Vth.

The delay circuit 300 has an input side to receive the charge sensitive amplifier output signal CS. The delay circuit 300 is configured to generate the delay circuit output signal DS with a first delay time DT1 after having received the charge sensitive amplifier output signal CS at the input side of the delay circuit 300.

FIG. 2A shows possible realization of the control circuit 500. The control circuit 500 comprises a second delay circuit 510 to generate a control signal s1 to switch the controllable switch 200 from the non-conductive state in the conductive state and vice versa. The second delay circuit 510 is configured to generate the control signal s1 with a second delay time DT2 after the control circuit 500 has detected the exceeding of the threshold value Vth of the charge stored in the capacitor 120.

The front-end electronic circuitry 10a is configured to act as a delay-line shaper. That is, the time-delayed version of the charge sensitive amplifier output signal, i.e. the delay circuit output signal DS, is subtracted from the charge sensitive amplifier output signal CS, thereby eliminating low frequency components, for example leakage and 1/f noise of the input stage. The delay time DT1 is chosen to be sufficiently long such that the complete charge collection of a charge caused by the input signal IS in the capacitor 120 is ensured. The signal IS may be generated from photon detector 20 that may be configured as a direct converter. The subtraction of the delay circuit output signal DS from the charge sensitive amplifier output signal CS results in an output signal OS having a narrow pulse. The front-end electronic circuitry 10a thus generates a narrow voltage pulse in response to an input signal IS being a current pulse.

If the delay time DT1 is set long enough to accommodate the worst-case transient response, the circuitry 10a exhibits low ballistic deficit. Moreover, due to the subtraction, the circuitry 10a is inherently insensitive to leakage currents and does not require baseline restoration for dynamic components.

The front-end electronic circuitry 10a is also equipped with a reset topology realized by the controllable switch 200 that is controlled by control circuit 500. The control circuit 500 comprises comparator circuit 530 being configured to compare a voltage of capacitor 120 with the threshold value Vth. When the voltage of capacitor 120 exceeds the threshold value Vth, the output signal of comparator circuit 530 changes its state so that a delay is started.

That means, after an input pulse IS with energy above a pulse threshold level determined by threshold value Vth is detected and the output of the comparator circuit 530 changes its state, a delay is triggered by delay circuit 510. As a result, control signal s1 is generated by delay circuit 510 with delay time DT2 after the output of the comparator circuit 530 has changed its value to switch controllable switch 200 into a conductive state.

In conclusion, after the delay time DT2 has elapsed, the feedback capacitor 120 is reset in that capacitor 120 is discharged via controllable switch 200 that is operated in the conductive state. As the trigger for delay circuit 510 is a threshold above the baseline, when the onset of the pulse has started, delay time DT2 may be selected to be shorter or equal than the transient delay time DT1 to maximize count-rate capability.

The front-end electronic circuitry 10a allows the generation of a pulse-shaped output signals OS, for example a voltage pulse, in response to an input current pulse IS. The controllable switch 200 is initially operated in the non-conductive/open state so that the capacitor 120 is charged in response to a current pulse IS applied to the input node I10. The output signal OS thus has a rising edge. After the delay time DT1 has elapsed, delay circuit 300 generates the delay circuit output signal DS. The amplitude of the delay circuit output signal DS is subtracted from the charge sensitive amplifier output signal CS so that the output signal pulse OS now shows a falling edge.

As soon as the charge stored in the capacitor 120 exceeds the threshold value Vth and delay time DT2 has elapsed, controllable switch 200 is switched into the conductive state by control circuit 500 so that the capacitor 120 is suddenly discharged and the output signal OS drops to the zero level.

Figure 2B:
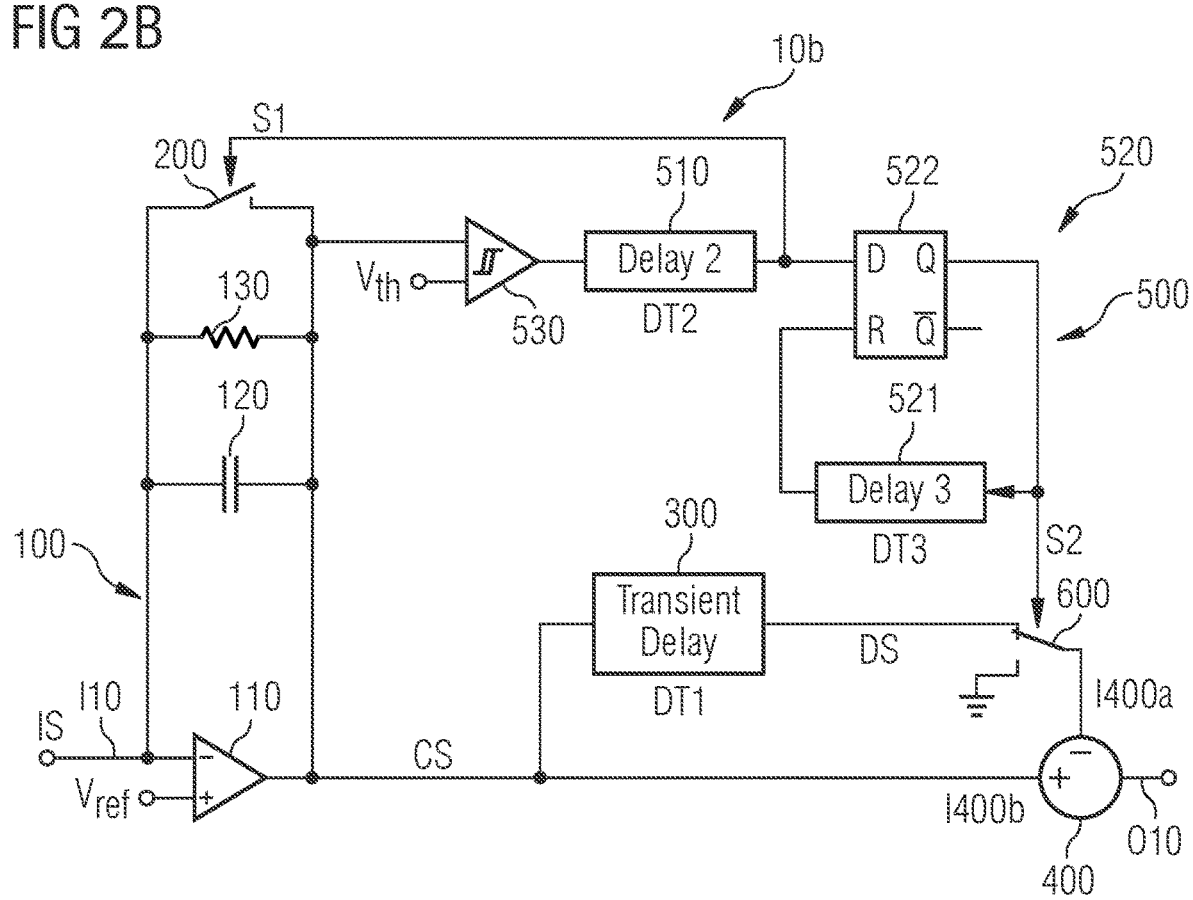
FIG. 2B shows a second, improved embodiment of a front-end electronic circuitry for a photon counting application having reduced ballistic deficit and high count-rate capabilities.

FIG. 2B shows an embodiment of a front-end electronic circuitry 10b being an improved modification of the configuration of FIG. 2A. As shown in FIG. 2B, the circuitry of FIG. 2A has been extended by a second controllable switch 600 to disconnect the delay circuit 300 from the output signal generation circuit 400. The output signal generation circuit 400 has a first input I400a connected to the second controllable switch 600, and a second input I400b connected to the output side of the amplifier circuit 110. The second controllable switch 600 is configured to be operated in a first state in which the second controllable switch 600 connects the delay circuit 300 to the first input I400a of the output signal generation circuit 400, and a second state in which the second controllable switch 600 disconnects the delay circuit 300 from the first input node I400a of the output signal generation circuit 400, and rather connects the first input node I400a to a reference potential VSS, for example a ground potential.

In order to control the first and second state of the second controllable switch 600, the control circuit 500 is extended by a control stage 520 comprising a third delay circuit 521 and a flip-flop 522. The control stage 520 is configured to generate a second control signal s2 with a first level to switch the second controllable switch 600 from the first state to the second state, and with a second level to switch the second controllable switch 600 from the second state to the first state. The control stage 520 is further configured to generate the first level of the second control signal s2 with a third delay time DT3 after having generated the second level of the second control signal s2.

In particular, the flip flop 522 generates the first level of the second control signal s2 after having received a state of the control signal s1 to switch the first controllable switch 200 in the conductive state. As a consequence, the second control switch 600 is switched to the reference potential. After having received the first level of the second control signal s2, the delay circuit 521 generates an output signal after delay time DT3 which triggers the flip flop 522 to generate the first level of the second control signal s2. The first level of the second control signal s2 causes the second controllable switch 600 to be switched back in the first state in which the second controllable switch 600 connects the delay circuit 300 to the output signal generation circuit 400.

Figure 3:
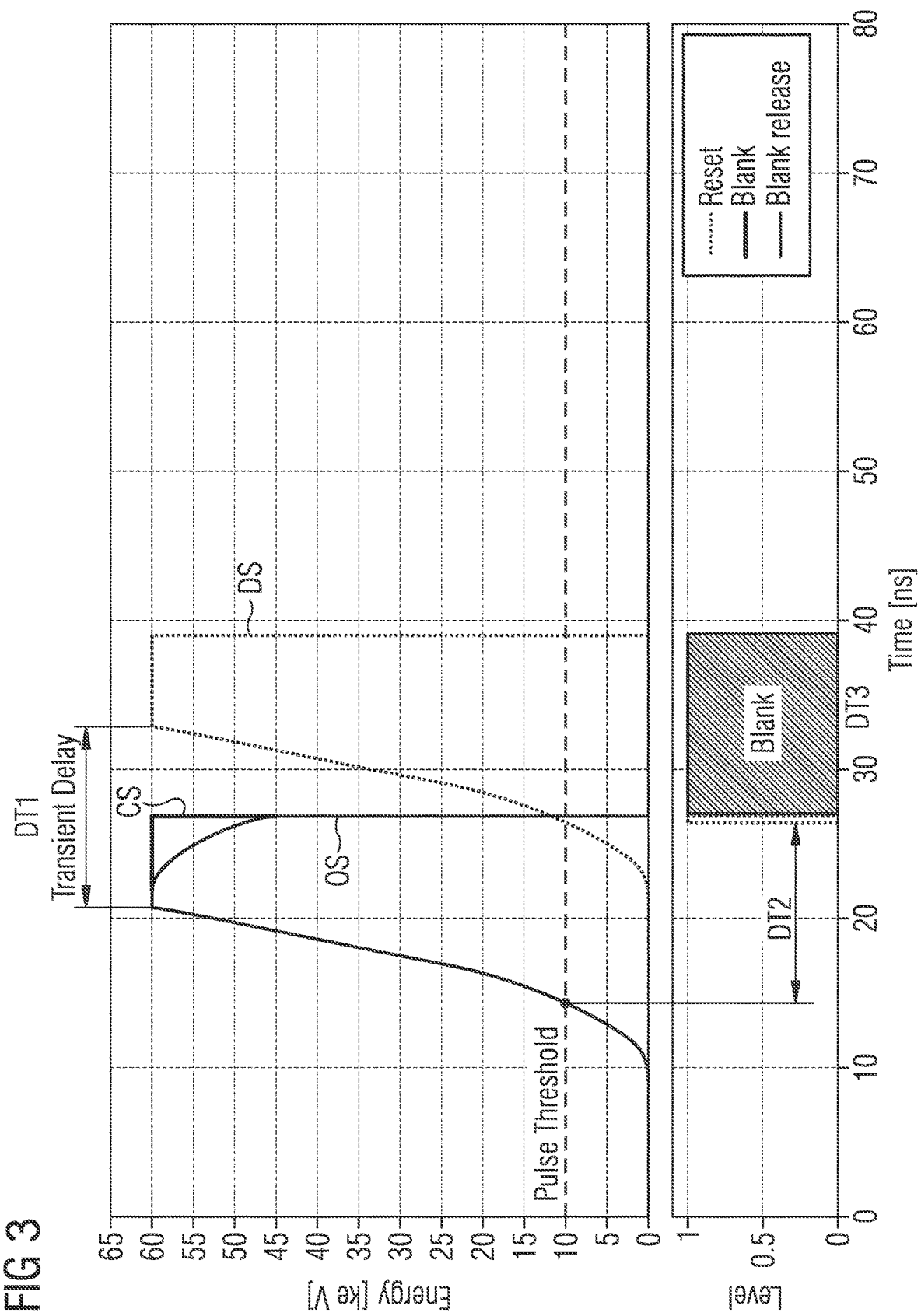
FIG. 3 illustrates the functionality of the second (improved) embodiment of the front-end electronic circuitry for a photon counting application.

FIG. 3 illustrates the functionality of the topology of the front-end electronic circuitry 10b of FIG. 2B. A photon impinging on the photon detector 20 causes the generation of a current pulse as input signal IS of circuitry 10b. The capacitor 120 is charged to a maximum value and the charge sensitive amplifier output signal CS as well as the output signal OS is generated with a rising edge. After the delay time DT1 has elapsed, the delay circuit output signal DS is subtracted from the charge sensitive amplifier output signal CS by the output signal generation circuit 400 so that the output signal OS shows a falling edge. After the charge stored in capacitor 120 exceeds a pulse threshold defined by threshold value Vth, delay circuit 510 generates control signal s1 so that the controllable switch 200 is switched into a conductive state. As a consequence, the capacitor 120 is suddenly discharged, and charge sensitive amplifier output signal CS drops to zero level.

According to the improved configuration of the front-end electronic circuitry 10b, the delayed version of the charge sensitive amplifier output signal, i.e. the delay circuit output signal DS, is disconnected from the output signal generation circuit 400 by controllable switch 600 for a time equal to delay time DT3. Controllable switch 600 is provided due to the reset of feedback capacitor 120. As explained above, the reset causes charge sensitive amplifier output signal CS to drop to zero level. The subtraction of the delay circuit output signal DS from the charge sensitive amplifier output signal CS by signal generation circuit 400 would lead to a large additional undershoot, as the delayed version of charge sensitive amplifier output signal is still propagating the signal prior to the reset. The second controllable switch 600 ensures that the propagation is not accounted for, eliminating the additional undershoot.

According to a preferred embodiment, the second controllable switch 600 is kept to the reference potential, for example to ground, for the same duration as delay time DT2, i.e. delay time DT2 is equal to delay time DT3. In this case, the output signal OS of circuitry 10b will follow the reset of charge sensitive amplifier 100 with no undershoots. Delay time DT3 during which the second controllable switch 600 is forced to the reference potential VSS is shown as "blank" in FIG. 3.

The blank period does not interfere with the pile-up behaviour. After the reset, charge sensitive amplifier 100 is ready to receive the next pulse. The fact that the delay-line is blanked does not play any role as long as it does not interfere with the transient delay time DT1 itself.

Of particular interest is the impact that the energy of an impinging photon and thus the input current pulse of input signal IS is so low that the reset is not triggered. The front-end electronic circuitries 10a and 10b, however, ensure that such events are still processed by the delay-line topology. That is, the output signal OS will result in a small pulse, which is very narrow and will not contribute to energy drifts other than by the probability of pile-up.

Figure 4:
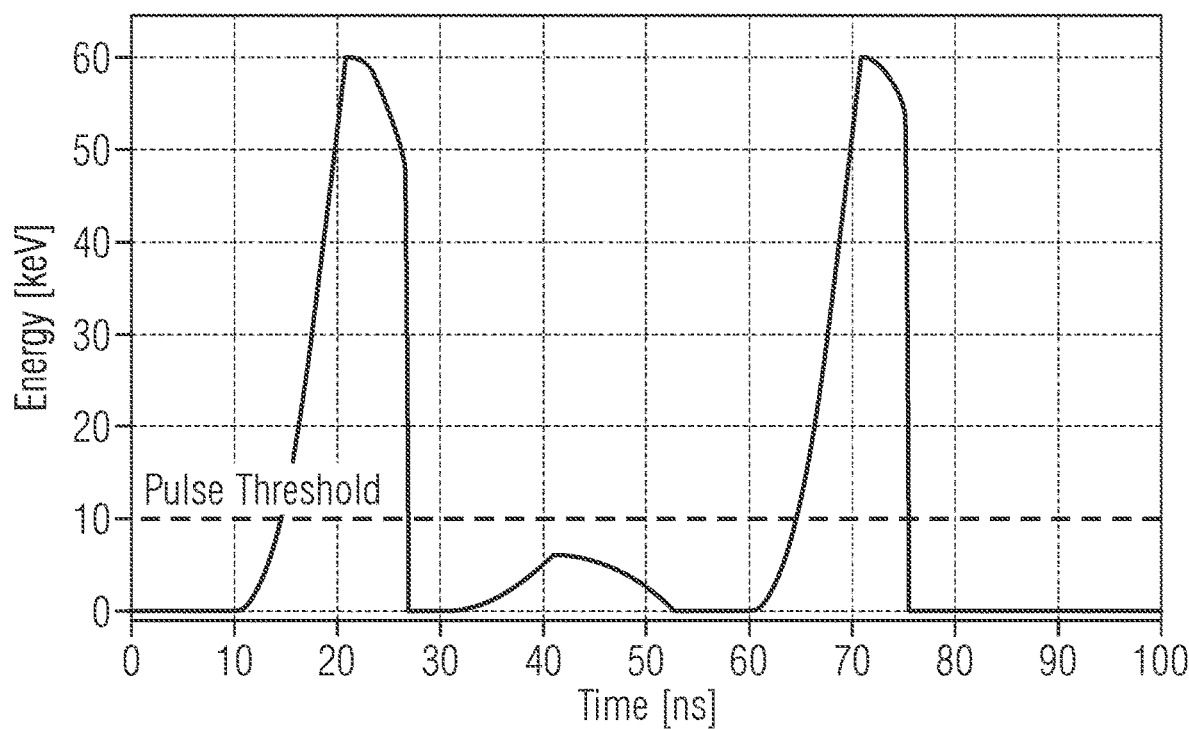
FIG. 4 illustrates a response of the proposed first embodiment of the front-end electronic circuitry to impinging photons below and above a pulse threshold value.

FIG. 4 shows such an event between two higher energy events. The second photon-impinging event, shown in FIG. 4 with only about 6 keV, for example, does not cross the pulse threshold level defined by threshold value Vth, and therefore it does not trigger a reset. However, the delay-line subtraction implemented in the front-end electronic circuitries 10a and 10b ensures that the pulse is confined to a very narrow interval. Without the delay-line topology, the charge sensitive amplifier 100 would accumulate the charge in capacitor 120 and cause an energy pedestal. The next pulse that is higher than the threshold value Vth would thus exhibit the wrong energy due to the energy pedestal.

If the front-end electronic circuitry is equipped with a feedback resistor 130, as shown in FIGS. 2A and 2B, a small residual undershoot may follow the low energy event. The second high energy event will therefore exhibit a marginal error. It has to be noted, however, that this residual undershoot does not propagate beyond the second pulse. The residual undershoot is energy-dependent. Since this only occurs for pulses which are below the pulse threshold, the error is constrained to very low levels of energy. However, as explained above, the feedback resistor 130 is optional so that with no feedback resistor, no residual undershoot will be present.

In conclusion, the respective embodiment of the front-end electronic circuitries 10a and 10b has negligible ballistic deficit with no flux-dependent energy distortion other than pulse pile-up. The use of the reset mechanism allows the inherent undershoots of delay-line shapers to be suppressed. Furthermore, the use of the delay-line shaper topology enables energy pedestals resulting from the reset event to be prevented.

The output signal OS generated by the front-end electronic circuitries 10a and 10b is inherently immune to any leakage or low frequency component with time constants significantly larger than the transient delay. Since the proposed configurations of front-end electronic circuitries 10a and 10b are equipped with the reset mechanism, saturation of the charge sensitive amplifier 110 is not an issue. Any voltage swing at the output of the charge sensitive amplifier caused by leakage and/or low frequency components, is constrained by the pulse threshold. If the level of the charge sensitive amplifier output signal CS goes above it, the circuit will self-reset. The charge sensitive amplifier 100 therefore does not strictly require a feedback resistor 130.

It should be further noted that kT/C noise caused by the reset mechanism is also compensated for because it will ultimately be removed by the subtraction of charge sensitive amplifier output signal CS and its delayed version DS.

The resulting count-rate capability of the front-end electronic circuitries 10a and 10b is inherently non-paralyzable. Both the reset action and the delay-line subtraction enforce a return to the baseline which yields a non-paralyzable characteristic.

The proposed configuration of the front-end electronic circuitries 10a and 10b offers excellent ballistic deficit performance. In particular, if two input pulses have the same charge, but the second pulse is 10% shorter in time, the output signal OS generated by the front-end electronic circuitries 10a and 10b delivers the same output amplitude in response to both input pulses, whereas a front-end electronic circuitry exhibiting ballistic deficit would deliver different pulse amplitudes in response to the inputs despite having the same charge.

Delay circuit 300 may be implemented by different types of circuits, for example cascaded amplifier with phase shift, delay-locked loop circuit, etc. The transient delay time DT1 may typically be between 5 nanoseconds and 25 nanoseconds, preferably between 7 ns and 12 ns. The transient delay time DT1 is always longer than the worst-case transient response for a regularly working direct converter pixel.

The pulse threshold defined by threshold value Vth is typically at the lowest possible energy level of impinging photons above the noise level to prevent false triggers, typically between three to five times the electronics' noise. Alternatively, the lowest threshold of the comparator system typically between 20 and 30 keV may also be used for the purpose of detecting impinging photons and trigger the reset.

The proposed configuration of front-end electronic circuitries 10a and 10b may be used for various photon counting applications such as computed tomography, security, baggage inspection and any other application requiring high photon counting rates and signal stability.

Figure 5:
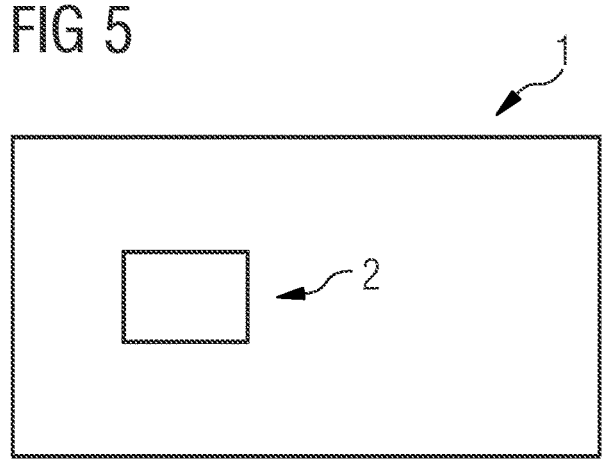
FIG. 5 shows a block diagram of a device for medical diagnostics.

FIG. 5 shows an example of an application, where a photon counting circuitry 2 being equipped with front-end electronic circuitries 10a or 10b is provided in a device 1 for medical diagnostics. The device may be configured, for example, as an X-ray apparatus or a computer tomography/computed tomography scanner.

The embodiments of the front-end electronic circuitry for a photon counting application disclosed herein have been discussed for the purpose of familiarizing the reader with novel aspects of the design of the front-end electronic circuitry. Although preferred embodiments have been shown and described, many changes, modifications, equivalents and substitutions of the disclosed concepts may be made by one having skill in the art without unnecessarily departing from the scope of the claims.

In particular, the design of the front-end electronic circuitry for a photon counting application is not limited to the disclosed embodiments, and gives examples of many alternatives as possible for the features included in the embodiments discussed. However, it is intended that any modifications, equivalents and substitutions of the disclosed concepts be included within the scope of the claims which are appended hereto.

Features recited in separate dependent claims may be advantageously combined. Moreover, reference signs used in the claims are not limited to be construed as limiting the scope of the claims.

Furthermore, as used herein, the term "comprising" does not exclude other elements. In addition, as used herein, the article "a" is intended to include one or more than one component or element, and is not limited to be construed as meaning only one.

The invention claimed is:

1. A front-end electronic circuitry for a photon counting application, comprising:
   an output node to provide an output signal,
   an input node to receive a input signal,
   a charge sensitive amplifier comprising an amplifier circuit having an input side being coupled to the input node and an output side to provide a charge sensitive amplifier output signal, and a capacitor being arranged in a feedback path between the input side and the output side of the amplifier circuit,
   a controllable switch being arranged in parallel to the capacitor, a delay circuit to provide a delay circuit output signal, the delay circuit output signal being a time-delayed representation of the charge sensitive amplifier output signal, an output signal generation circuit being coupled to the output node to provide the output signal, wherein the output signal generation circuit is configured to generate the output signal by subtracting the delay circuit output signal from the charge sensitive amplifier output signal.

2. The front-end electronic circuitry of claim 1, wherein the delay circuit has an input side to receive the charge sensitive amplifier output signal, wherein the delay circuit is configured to generate the delay circuit output signal with a first delay time after having received the charge sensitive amplifier output signal at the input side of the delay circuit.

3. The front-end electronic circuitry of claim 1, wherein the charge sensitive amplifier and the capacitor are arranged so that, when the input signal is formed as a current pulse, a charge is stored in the capacitor, the charge being dependent on the current pulse of the input signal.

4. The front-end electronic circuitry of claim 1, wherein the controllable switch is operated in a non-conductive state and a conductive state, wherein the controllable switch and the capacitor are arranged so that the capacitor is charged, when the controllable switch is operated in the non-conductive state, and the capacitor is discharged, when the controllable switch is operated in the conductive state.

5. The front-end electronic circuitry of claim 1, comprising:

a control circuit being configured to monitor the charge stored in the capacitor and to control the controllable switch in dependence on the charge stored in the capacitor.

6. The front-end electronic circuitry of claim 5, wherein the control circuit is configured to switch the controllable switch from the non-conductive state in the conductive state after a delay, when the control circuit detects that the charge stored in the capacitor exceeds a threshold value.

7. The front-end electronic circuitry of claim 5, wherein the control circuit comprises a second delay circuit to generate a control signal to switch the controllable switch from the non-conductive state in the conductive state, wherein the second delay circuit is configured to generate the control signal with a second delay time after the control circuit has detected the exceeding of a threshold value of the charge stored in the capacitor.

8. The front-end electronic circuitry of claim 7, wherein the delay circuit and the second delay circuit are configured such that the second delay time is shorter than or equal to the first delay time.

9. The front-end electronic circuitry of claim 1 comprising:

a second controllable switch to disconnect the delay circuit from the output signal generation circuit, wherein the output signal generation circuit has a first input connected to the second controllable switch and a second input connected to the output side of the charge sensitive amplifier circuit.

10. The front-end electronic circuitry of claim 9, wherein the second controllable switch is configured to be operated in a first state in which the second controllable switch connects the delay circuit to the first input of the output signal generation circuit, and a second state in which the second controllable switch disconnects the delay circuit from the first input node of the output signal generation circuit, and connects the first input node of the output signal generation circuit to a reference potential.

11. The front-end electronic circuitry of claim 9, wherein the control circuit comprises a control stage to generate a second control signal with a first level to switch the second controllable switch from the first state to the second state, and with a second level to switch the second controllable switch from the second state to the first state, wherein the control stage is configured to generate the first level of the second control signal with a third delay time after having generated the second level of the second control signal.

12. The front-end electronic circuitry of claim 11, wherein the third delay circuit is configured such that the third delay time is equal or longer than the second delay time.

13. The front-end electronic circuitry of claim 1, wherein the integrator circuit comprises a resistor being connected in parallel to the capacitor.

14. A photon counting circuitry, comprising:

a front-end electronic circuitry according to claim 1, a photon detector having a photon sensitive area, the photon detector being configured to generate a current pulse, when a photon hits the photon sensitive area, an energy discriminator being connected to the output node of the front-end electronic circuitry, wherein the photon detector is connected to the input node of the front-end electronic circuitry so that the current pulse generated by the photon detector circuitry is applied to the input node of the front-end electronic circuitry, when the photon hits the photo sensitive area of the photon detector, wherein the front-end electronic circuitry is configured to generate a voltage pulse at the output node of the front-end electronic circuitry, when the current pulse is applied to the input node of the front-end electronic circuitry, wherein the energy discriminator is configured to generate a digital signal in dependence on a level of the voltage pulse.

15. A device for medical diagnostics, comprising:

the photon counting circuitry of claim 14, wherein the device is configured as an X-ray apparatus or a computer tomography.

* * * * *